(12) United States Patent
Michels et al.

(10) Patent No.: US 7,594,971 B2
(45) Date of Patent: Sep. 29, 2009

(54) METHOD OF CLEANING AND STERILIZING MEDICAL INSTRUMENTS

(75) Inventors: Winfried Michels, Warburg (DE); Michael Pieper, Theda-Wiedenbrueck (DE)

(73) Assignee: Miele & Cie KG, Guetersloh (DE)

( * ) Notice: Subject to any disclaimer, the term of this patent is extended or adjusted under 35 U.S.C. 154(b) by 0 days.

(21) Appl. No.: 10/994,127

(22) Filed: Nov. 19, 2004

(65) Prior Publication Data

US 2005/0183748 A1 Aug. 25, 2005

(51) Int. Cl.
*B08B 3/04* (2006.01)
(52) U.S. Cl. ............... 134/26; 134/18; 134/29; 134/30; 134/32; 134/34; 134/36; 134/56 D; 134/58 D; 134/58 R; 510/220; 436/28; 436/34
(58) Field of Classification Search .......... 436/34, 436/28; 134/18, 26, 29, 30, 32, 34, 36, 56 D, 134/58 D, 58 R; 510/220
See application file for complete search history.

(56) References Cited

U.S. PATENT DOCUMENTS

| | | | | |
|---|---|---|---|---|
| 3,519,379 | A * | 7/1970 | Blomeyer et al. ............... | 8/111 |
| 4,118,189 | A * | 10/1978 | Reinwald et al. ............... | 8/137 |
| 4,592,785 | A * | 6/1986 | Reinert et al. ................. | 134/18 |
| 4,994,200 | A | 2/1991 | Disch et al. | |
| 5,698,504 | A * | 12/1997 | Christie et al. ............... | 510/220 |
| 5,747,438 | A * | 5/1998 | MacBeath ................... | 510/224 |
| 6,159,922 | A | 12/2000 | Williams .................... | 510/372 |
| 6,200,351 | B1 * | 3/2001 | Schleinig et al. ............. | 8/115.6 |
| 6,239,091 | B1 * | 5/2001 | Tartakovsky et al. ......... | 510/220 |
| 6,723,687 | B2 * | 4/2004 | Clare ......................... | 510/101 |
| 2003/0148906 | A1 * | 8/2003 | Alam et al. .................. | 510/221 |
| 2004/0167048 | A1 * | 8/2004 | Sunder et al. ............... | 510/220 |
| 2004/0194810 | A1 * | 10/2004 | Strothoff et al. ........... | 134/25.2 |
| 2005/0130863 | A1 * | 6/2005 | Blagg et al. ................. | 510/375 |

FOREIGN PATENT DOCUMENTS

| | | |
|---|---|---|
| DE | 3327466 | 2/1985 |
| DE | 3601744 * | 7/1987 |
| DE | 38 43 992 C2 | 7/1990 |
| DE | 4219620 | 12/1993 |
| DE | 43 42 573 A1 | 6/1995 |
| DE | 4342573 * | 6/1995 |
| DE | 19626872 | 1/1998 |
| EP | 0268227 | 5/1988 |
| EP | 1138335 | 10/2001 |
| EP | 1260234 | 11/2002 |
| WO | WO 01/47565 A2 | 5/2001 |

OTHER PUBLICATIONS

Kathy Antiloga et al.: Prion Disease and Medical Devices; ASAIO Journal 2000, pp. 569-572.

* cited by examiner

*Primary Examiner*—Sharidan Carrillo
(74) *Attorney, Agent, or Firm*—Darby & Darby

(57) ABSTRACT

A novel method of cleaning and disinfecting organically contaminated articles such as, for instance, medical instruments, wherein the cleaning cycle consists of two sections divided by removal and replenishing the cleaning liquid, in each section of which the temperature of the cleaning liquid is raised to and maintained at between 40° C. and 60° C. for a predetermined time and the pH-value is raised to between 8.5 and 12 by adding an alkaline cleaning agent. During the second section a low-molecular peroxide compound is added to the cleaning liquid after the cleaning agent.

15 Claims, No Drawings

METHOD OF CLEANING AND STERILIZING MEDICAL INSTRUMENTS

BACKGROUND OF THE INVENTION

Field of the Invention

The invention, in general, relates to a method of cleaning and disinfecting organically contaminated articles and, more particularly, to a method of the kind referred to for cleaning and sterilizing medical instruments in which the water-requiring pre-rinsing and cleaning cycles of the program are carried out in a rinsing compartment of a program-controlled machine wherein a fluid is heated to a temperature of between 40° C. and 60° C., preferably 55° C., to which an alkaline cleaning agent is added such that the resultant pH-value is between 8.5 and 12.

German patent specification DE 43 42 573 A1 discloses a method of cleaning and disinfecting or sterilizing laboratory and surgical instruments which is carried out in a program-controlled machine which is similar to a dishwasher provided with a rinsing container or compartment. The known method serves to process the instruments and includes such water-requiring rinsing programs as pre-rinsing, cleaning, neutralizing, intermediate rinsing and thermal sterilization. Optionally, either or both of the pre-rinse and intermediate rinse program cycles may be switched off. For the removal of particularly coarse blood soiling and for soaking slightly dried residues attached to the instruments, the program is initiated with cold and softened water by a short pre-rinse cycle lasting 1 to 3 minutes and terminating by removal of the soiled liquid. During the ensuing cleaning program cycle, softened water is first filled into the rinsing compartment heated to between 45° C. and 60° C., preferably 55° C. While the water is being heated an alkaline cleaner is added to it. The composition of the cleaner and the amount of it added to the water are such that a pH-value is reached between 8.5 and 12. In order for the cleaner to become optimally effective, the predetermined maximum temperature is maintained for several minutes before the cleaning liquid is removed. For neutralizing residual alkaline fluid on the rinsed instruments, a neutralizing cycle is then initiated during which the instruments are rinsed in an acidic neutralizing agent. Following the neutralizing cycle and removal of the fluid, one or more rinsing cycles ensue, each with fresh water, depending upon the degree of contamination of the alkaline fluid and instruments. After renewed fluid removal the medical instruments are treated in a thermal sterilization cycle in water heated to 90° C. Preferably, this cycle is carried out in fully de-ionized water.

The problem inherent in such a cleaning and sterilization process is that it is hard to dissolve and poorly visible residue such as, in particular, fibrinous residue as cross-linked blood components, tends to adhere to the treated instruments. This is particularly immanent in connection with coagulation instruments. Hence, in terms of standardizing the cleaning results on a high level and as a precondition for safety of the sterilization, the known method of treating instruments needs to be improved. In this connection, particular care is to be taken in respect of a preventing the transmittal of infectious prions which may cause Creutzfeld-Jacob-disease or its new variant and which may be embedded in the fibrinous residue are adhere to the surface of the instruments because of their high affinity to metal.

The fibrinous residue or prion-proteins could possibly be removed by a very strong alkaline cleaner with a pH-value in excess of 12 is added to an extremely hot clean fluid. However, such an approach would damage the material of some of the instruments to be cleaned. Some instrument materials such as, for instance, optical glasses and aluminum, are particularly sensitive.

Th use of a fluid concentrate for removing organic contaminations is known from German patent specification DE 38 43 992 C2. As an active oxygen compound the concentrate contains one or more salts of peroxosulfuric acid. Based on its total molecular weight, such a high molecular compound contains but a small proportion of free oxygen radicals. In order to obtain a quantity of active oxygen sufficient for cleaning and sterilizing medical instruments it would be necessary to add large quantities of this fluid concentrate. If used in the cleaning program cycle known from German patent specification DE 43 42 573 A1, the free oxygen radicals would combine with the dirt particles dissolved in the fluid and would no longer be available to remove the contamination from the instruments.

The use of peracetic acid for disinfection purposes is known. The acidic solutions resulting from the process would denature the proteins and lead to a strong incrustation.

Proceeding from the above-described method of cleaning and disinfecting medical instruments, it is an object of the invention to optimize the cleaning of instruments including an assured removal of cross-linked difficult to dissolve and protein-containing contaminations from the surface of instruments under conditions gentle to the materials as well as to destroy prion proteins.

In accordance with the invention, the object is accomplished by subdividing the cleaning program cycle into two partial cycles with the cleaning liquid being changed between the first and second partial cycles and a low-molecular peroxide compound being added to the fluid in the second partial cycle, in addition to the alkaline cleaner. At a pH-value above 8.5 the low-molecular peroxide decomposes spontaneously and immediately releases large quantities of active oxygen. Since as a result of the preceding change of cleaning liquid no more dirt particles are present, the active oxygen acts on the resistant contaminants on the instruments; even the proteins causing the new variant Creutzfeld-Jacobs infections are oxidatively destroyed and converted into compounds easily dissolved in water and which may thus simply rinsed away with the cleaning liquid.

In an advantageous improvement of the method, the cleaning agent used is free of tensides to prevent an unnecessary consumption or destruction of active oxygen.

Moreover, it is advantageous to add the low-molecular peroxide compound after the alkaline cleaning agent has been added to the liquid. In this manner, the alkaline environment is created initially which is necessary for the release of the free oxygen radicals. Moreover, the development of a neutral or acidic environment is prevented in which the proteins denature and thus more strongly adhere to the instruments.

In a useful embodiment of the method of cleaning and disinfecting medical instruments the low-molecular peroxide compound is a solution of peracetic acid or of hydrogen peroxide.

An advantageous improvement of the teaching in accordance with the invention provides for adding the low-molecular peroxide compound prior to the liquid having attained its final temperature. Since the peroxide releases oxygen as soon as it is present in the cleaning liquid, the measure mentioned leads to a reduction in the necessary duration of the cleaning operation.

DETAILED DESCRIPTION OF THE PREFERRED EMBODIMENT

The method in accordance with the invention for cleaning and disinfecting medical instruments such as, for instance, laboratory and surgical instruments, e.g. tongues, pliers, scissors, rigid and/or flexible endoscopes, their optics and the like, will be described in greater detail. A program-controlled dishwasher-like machine (hereafter "machine") is used for practicing the invention. As is known, the machine is provided with a support for the instruments and rinsing compartment with a moveable trolley. Basically, the method to be described can also be implemented in program sequences of cleaning machines used for cleaning, rinsing and thermally disinfecting motors and drive systems of the kind used in orthopedic surgery and/or dental medicine.

The machine for practicing the method in accordance with the invention uses cleaning liquids for cleaning and disinfecting which can be heated to predetermined temperatures (cleaning and disinfection temperatures) and to which cleaning agents may be admixed if required. The rinsing container is filled with the cleaning liquid, i.e. cold or warm soft service water or fresh water which may be softened water. In addition, the machine is provided with a connector for fully deionized water. The cleaning liquid filled into the compartment is agitated during water-requiring program cycles and is sprayed onto the instruments to be cleaned and thereafter disinfected.

The method in accordance with the invention for cleaning and disinfecting comprises consecutive water-requiring pre-rinsing, cleaning, neutralizing, intermediate rinsing and thermal disinfection program cycles. Intermediate rinsing cycles may repeatedly be activated by the program control. Also, for purposes of conserving water and energy, the intermediate rinsing may be deactivated depending upon the degree of contamination of the instruments to be cleaned.

For rinsing off coarse contaminants of the instruments and easily removable blood, the pre-rinsing program cycle is performed as the first step of the method in which cold softened water is fed to the rinsing compartment of the machine. There will be no heating since in cold water the contaminants to be removed foams less. After pre-rinsing for 1 to 3 minutes and changing the water, a first heated cleaning cycle is executed during which the cleaning liquid is heated to a final temperature of 55° C. Upon attaining a temperature of about 40° C., an alkaline cleaning agent is automatically added as a processing agent. The amount of the cleaner and its alkalinity are measured such that an pH-value of 11 to 11.5 is realized which is optimal for releasing the contaminants attached to the instruments. Preferably, the cleaning agent contains a silicate for protecting the materials to be processed and it is also free of tensides. After the final temperature of 55° C. has been reached it is maintained for 5 to 10 minutes while the cleaning process continues. Thereafter, the cleaning liquid is removed.

Thereafter, softened water is again filled into the rinsing compartment. In addition, at 40° C. alkaline cleaning agent is again added with the consequential adjustment of the pH-value to 11 to 11.5. After adding the alkaline cleaner a low-molecular peroxide compound is additionally added to the cleaning liquid.

By adjusting the pH-value to between 8.5 and 12 by an alkaline cleaning agent, the peroxide in the cleaning fluid decays spontaneously and a high oxidation potential becomes available immediately. Such oxidation causes resistant and difficult to dissolve contaminants such as fibrin residue as well as coagulations on high frequency surgical instruments which remain attached to the materials to be cleaned as invisible layers, to be destroyed or inactivated and to be converted compounds easily dissolved in water. In order to inactivate as much of such contamination as possible within a short time and to convert them into compounds quickly soluble in water, the cleaning liquid is heated to a final temperature of 55° C. This temperature is sufficiently low to prevent denaturing of protein-containing residues and to ensure a rapid release of oxygen from the peroxide. In order to destroy all proteinaceous contaminants and to release them from the rinsed material, the final temperature is maintained constant for about 10 minutes before the cleaning liquid with the resistant released contaminants is removed.

Suitable processing agent are, in particular, hydrogen peroxide or a solution of peracetic acid since they are low-molecular and are, therefore, capable of releasing a high proportion of their total mass as active oxygen. They are commercially available and cost-efficient. Hydrogen peroxide is to be preferred because, unlike peracetic acid, its neutrality does not cause a shift of the pH-value of the cleaning liquid set by the cleaning agent. Another advantage of hydrogen peroxide is that it decomposes into water and oxygen and the remaining residues do not, therefore, have to be subjected to a risk analysis.

After completion of the last cleaning step, the neutralizing and thermal disinfection steps are invoked which need not be described in view of the fact that they are well known.

What is claimed is:

1. A method of cleaning and disinfecting organically contaminated articles, comprising the steps of:
   a) placing the articles into a cleaning compartment of a program-controlled cleaning machine;
   b) adding the first cleaning liquid to the cleaning compartment;
   c) heating the first cleaning liquid to a temperature of between 40° C. and 60° C.;
   d) raising the pH-value of the first cleaning liquid in the cleaning compartment to between 8.5 and 12 by adding a first alkaline cleaning agent to the first cleaning liquid;
   e) removing the first cleaning liquid and the first alkaline cleaning agent after a first predetermined time;
   f) adding a second cleaning liquid to the cleaning compartment;
   g) heating the second cleaning liquid to a temperature of between 40° C. and 60° C.;
   h) raising the pH-value of the second cleaning liquid in the cleaning compartment to between 8.5 and 12 by adding a second alkaline cleaning agent to the second cleaning liquid;
   i) adding a peroxide compound to the second cleaning liquid after step h) so as to release active oxygen from the peroxide compound, the peroxide compound being added only after the adding of the second alkaline cleaning agent to the second cleaning liquid; and
   j) removing the second cleaning liquid, the second alkaline cleaning agent and the peroxide compound after a second predetermined time, wherein steps c) through e) are performed sequentially and steps g) through j) are performed sequentially.

2. The method of claim 1, wherein step b) is preceded by rinsing the articles.

3. The method of claim 1, wherein at least one of the first and the second cleaning liquids is softened water.

4. The method of claim 1, wherein the first predetermined time is from 5 to 10 minutes.

5. The method of claim 1, wherein the low-molecular peroxide compound is a solution of peracetic acid.

6. The method of claim 1, wherein the low-molecular peroxide compound is a solution of hydrogen peroxide.

7. The method of claim 1, wherein the temperature of the second cleaning liquid is raised after the peroxide compound has been added.

8. The method of claim 1, wherein the second predetermined time is from 5 to 10 minutes.

9. The method of claim 1, further comprising agitating the first and the second cleaning liquids.

10. The method of claim 2, wherein the rinsing is performed in softened water.

11. The method of claim 3, wherein the softened water is deionized.

12. The method of claim 4, wherein the pH-value in step d) and step h) is between 11.5 and 12.

13. The method of claim 10, wherein the third predetermined time is from 1 to 3 minutes.

14. The method of claim 12, wherein at least one of the first and second cleaning liquids is heated to about 55° C.

15. The method of claim 12, wherein at least one of the first and the second alkaline cleaning agents is free of tensides.

* * * * *